(12) United States Patent
Lee et al.

(10) Patent No.: US 11,624,087 B2
(45) Date of Patent: Apr. 11, 2023

(54) COMPOSITION FOR DETECTING NUCLEIC ACID AND COLORIMETRIC SIGNAL ENHANCEMENT METHOD OF DETECTING NUCLEOTIDE USING THEREOF

(71) Applicant: Korea Research Institute of Chemical Technology, Daejeon (KR)

(72) Inventors: Jieon Lee, Daejeon (KR); Woo-keun Kim, Daejeon (KR); Sangwoo Lee, Daejeon (KR); Seokjoo Yoon, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 98 days.

(21) Appl. No.: 16/917,135

(22) Filed: Sep. 22, 2020

(65) Prior Publication Data
US 2021/0002695 A1 Jan. 7, 2021

(30) Foreign Application Priority Data
Jul. 1, 2019 (KR) ........................ 10-2019-0078679

(51) Int. Cl.
*C12Q 1/682* (2018.01)

(52) U.S. Cl.
CPC .................... *C12Q 1/682* (2013.01)

(58) Field of Classification Search
CPC .............. C12Q 1/682; C12Q 2521/345; C12Q 2563/125
See application file for complete search history.

(56) References Cited

U.S. PATENT DOCUMENTS

2016/0289733 A1\* 10/2016 Li ........................ C12Q 1/6844

OTHER PUBLICATIONS

Luo et al. Chemiluminescence biosensors for DNA detection using graphene oxide and a horseradish peroxidase-mimicking DNAzyme. Chem. Commun. (2012) 48:1126-1128.\*
Wan et al., Target-assisted self-cleavage DNAzyme probes for multicolor simultaneous imaging of tumor-related microRNAs with signal amplification, Royal Society of Chemistry, Feb. 19, 2019, pp. 3278-3281 vol. 55.
Zhao et al., Graphene-DNAzyme Based Biosensor for Amplified Fluorescence "Turn-On" Detection of Pb2p with a High Selectivity, Analytical Chemistry, Jun. 3, 2011, pp. 5062-5066 vol. 83.
Zhang et al., Optimizing the specificity of nucleic acid hybridization, Nature Chemistry, 2012, pp. 208-214, vol. 4.
Kim et al., The Structural Influence of Graphene Oxide on Its Fragmentation during Laser Desorption/Ionization Mass Spectrometry for Efficient Small-Molecule Analysis, Chemistry European Journal, 2015, pp. 7217-7223, vol. 21.

\* cited by examiner

*Primary Examiner* — David C Thomas
(74) *Attorney, Agent, or Firm* — Klarquist Sparkman, LLP

(57) ABSTRACT

The present invention relates to a composition for detecting nucleic acid comprising duplex molecular beacon and graphene oxide and a colorimetric signal enhancement method of detecting nucleic acid using the same. According to the composition, kit and method for detecting nucleic acid of the present invention, a complex can be formed by adsorbing a single strand having a DNAzyme sequence dissociated from the conjugate of a duplex molecular beacon and a target nucleic acid to the graphene oxide surface, and separated, and a colorimetric signal amplified therefrom can be induced, so that a very low concentration of target nucleic acid can be detected with high efficiency and the target nucleic acid can be detected quickly and easily in seconds. Therefore, a new colorimetric target nucleic acid detection system capable of point of care testing (POCT) can be provided.

10 Claims, 15 Drawing Sheets
(9 of 15 Drawing Sheet(s) Filed in Color)
Specification includes a Sequence Listing.

STEP 1

STEP 2

Control

GONET-assisted

COMPOSITION FOR DETECTING NUCLEIC ACID AND COLORIMETRIC SIGNAL ENHANCEMENT METHOD OF DETECTING NUCLEOTIDE USING THEREOF

CROSS-REFERENCE TO RELATED APPLICATION

This application claims the benefit of priority from Korean Patent Application No. 10-2019-0078679 filed Jun. 1, 2019, the contents of which are incorporated herein by reference.

BACKGROUND OF THE INVENTION

1. Field of the Invention

The present invention relates to a composition for detecting nucleic acid comprising duplex molecular beacon and graphene oxide and a colorimetric signal enhancement method of detecting nucleic acid using the same.

2. Description of the Related Art

MicroRNAs (miRNAs) are 17-25 nucleotides non-coding RNAs involved in RNA silencing and post-transcriptional regulation of gene expression. Numerous studies have confirmed the expression of specific miRNAs in specific tissues and cell types. Their abnormal expression is associated with a variety of serious diseases such as cancer, viral infections, immune diseases and neurodegenerative disorders. For example, miRNA-21, which is known to have oncogenic functions, is constantly overexpressed in various types of malignant tumors such as breast cancer, pancreatic cancer, and hepatocellular carcinoma. In 2008, some tumor-derived miRNAs with high stability were found in serum and plasma of cancer xenograft mice. Tumor-specific miRNAs are also detected in patients' clinical samples, and thus miRNAs are attracting attention as promising non-invasive biomarkers.

In general, real-time PCR and miRNA microarray have been conventionally used for quantitative detection of miRNA. However, due to complicated procedures and expensive reagents and devices, there were limitations in actual clinical applications. In order to solve the above problems, there have been many technical and scientific attempts to construct a simple and fast detection platform that can be applied to a point-of-care testing (POCT) system. Many miRNA detection systems based on various techniques combining colorimetric, fluorescent, surface plasmon resonance and electrochemical methods and sophisticated signal amplification methods have been proposed in recent decades. Among them, the naked eye colorimetric method using the unique optical properties of nanomaterials or the enzymatic reaction of biomolecules has received considerable attention for miRNA POCT due to its simplicity and low cost.

DNAzyme (Dz), adopting the G-quadruplex structure, is one of the most common signal generators used in unlabeled colorimetric methods, and can exhibit a peroxidase-like activity in the presence of hemin. This catalytic DNA molecule has already been applied to numerous detection systems with various signal generators based on its thermal stability, ease of functionality and cost effectiveness.

Graphene oxide is an inexpensive nanomaterial that can be synthesized in large quantities. It has both hydrophilic and hydrophobic parts, and is used in various biosensor applications because it interacts strongly with single-stranded nucleic acids compared to double-stranded nucleic acids. In biosensors, graphene oxide generally exhibits strong affinity to single-stranded nucleic acids (ssNAs) through pi-pi stacking or hydrogen bonding interactions, and thus serves as a material for high-efficiency separation of ssNAs. However, despite the high applicability of graphene oxide in POCT systems, few colorimetric analysis methods have been developed compared to fluorescent or electrochemical applications. In most cases, the target generally changed color of the supernatant by causing aggregation or disaggregation of graphene oxide with a colorimetric signal generator (eg, gold nanoparticles, hemin, peroxidase DNAzyme).

In efforts to develop a noble colorimetric target nucleic acid detection system, the present inventors confirmed that the newly designed duplex molecular beacon and graphene oxide can be used to amplify the detection signal to detect the target nucleic acid with high efficiency, and thus they can be used for an easy and fast point-of-care testing (POCT) system, resulting in the completion of the present invention.

SUMMARY OF THE INVENTION

It is an object of the present invention to provide a colorimetric target nucleic acid detection system capable of easy and fast point-of-care testing (POCT) and detecting a target nucleic acid with high efficiency by amplifying a detection signal.

It is another object of the present invention to provide a method for detecting a target nucleic acid with an amplified detection signal using the system.

To achieve the above objects, the present invention provides a composition for detecting nucleic acid with an amplified detection signal comprising graphene oxide, duplex molecular beacon and DNAzyme cofactor, wherein the duplex molecular beacon is formed by complementarily conjugating the first single strand containing the target nucleic acid binding sequence and the second single strand containing the DNAzyme sequence at least in part, and the second single strand is separated from the first single strand and adsorbed to graphene oxide to form a graphene oxide complex in the presence of the target nucleic acid.

The present invention also provides a method for detecting a target nucleic acid with an amplified detection signal comprising the following steps:

obtaining a mixture by mixing a sample containing a target nucleic acid and a duplex molecular beacon;

adding graphene oxide to the mixture; and obtaining a concentrated graphene oxide complex by filtering or separating the mixture.

In addition, the present invention provides a kit for detecting nucleic acid with an amplified detection signal comprising graphene oxide, duplex molecular beacon and DNAzyme cofactor, wherein the duplex molecular beacon is formed by complementarily conjugating the first single strand containing the target nucleic acid binding sequence and the second single strand containing the DNAzyme sequence at least in part, and the second single strand is separated from the first single strand and adsorbed to graphene oxide to form a graphene oxide complex in the presence of the target nucleic acid.

Advantageous Effect

According to the composition, kit and method for detecting nucleic acid of the present invention, a complex can be formed by adsorbing a single strand having a DNAzyme sequence dissociated from the binding of a duplex molecular beacon and a target nucleic acid to the graphene oxide surface, and separated, and a colorimetric signal amplified therefrom can be induced, so that a very low concentrations of target nucleic acid can be detected with high efficiency and the target nucleic acid can be detected quickly and easily in seconds. Therefore, a new colorimetric target nucleic acid detection system capable of point of care testing (POCT) can be provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE PREFERRED EMBODIMENTS

Figure 1:
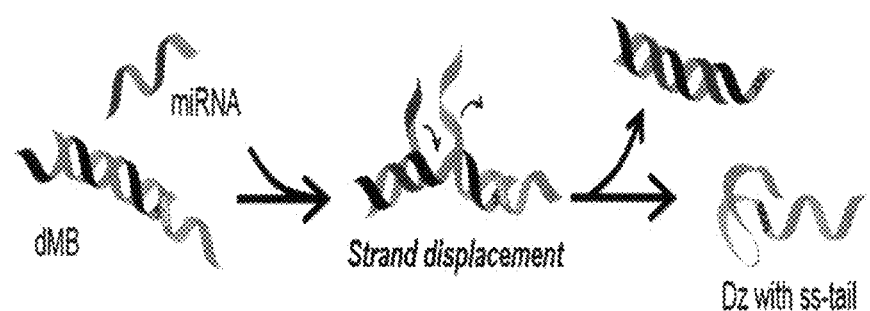
FIG. 1 is a diagram showing the outline of a GONET-based colorimetric miRNA detection method. Step 1 is an activation process of DNAzyme by miRNA, and step 2 is a signal amplification process by GONET.
Figure 1:
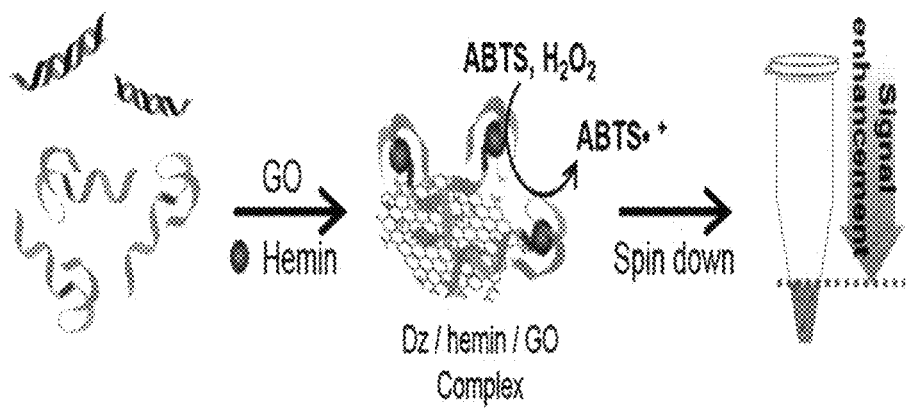

Hereinafter, the present invention is described in detail.

The present invention provides a composition for detecting nucleic acid with an amplified detection signal comprising graphene oxide, duplex molecular beacon and DNAzyme cofactor, wherein the duplex molecular beacon is formed by complementarily conjugating the first single strand containing the target nucleic acid binding sequence and the second single strand containing the DNAzyme sequence at least in part, and the second single strand is separated from the first single strand and adsorbed to graphene oxide to form a graphene oxide complex in the presence of the target nucleic acid.

In one aspect of the present invention, the first single strand can include a target nucleic acid binding sequence, and can also include a DNAzyme blocking sequence (Dz blocking element).

Herein, the target nucleic acid binding sequence can be understood as a sequence capable of complementarily binding at least a portion of a target nucleic acid sequence, and the first single strand binds to the target nucleic acid through the complementary binding of the target nucleic acid binding sequence and the target nucleic acid and is separated from the second single strand.

In addition, the DNAzyme blocking sequence can be understood as a sequence that inhibits the DNAzyme sequence of the second single strand from becoming an active form, and the DNAzyme blocking sequence can be a sequence at least partially complementary to the DNAzyme sequence. The active form of the DNAzyme sequence refers to a structure capable of functioning as DNAzyme, and can be a nucleic acid quadruplex structure, for example, the nucleotide quadruplex structure can be a G-quadruplex structure.

In one aspect of the present invention, the second single strand comprises a DNAzyme sequence, and can selectively include a sequence complementary to the target nucleic acid binding sequence.

Herein, the DNAzyme sequence refers to a sequence that functions as DNAzyme or a sequence in which a nucleic acid construct capable of functioning as DNAzyme can be formed, for example, a sequence in which a nucleic acid quadruplex structure can be formed, and in one embodiment, a sequence in which a G-quadruplex structure can be formed.

The said "DNAzyme" generally refers to a nucleic acid molecule having an enzymatic activity, for example, the DNAzyme can have a peroxidase activity.

When the duplex molecular beacon is bound to the target nucleic acid, the second single strand is released from the duplex molecular beacon, where at least a part of the second single strand can form a G-quadruplex structure. Also, at least a part of the second single strand can have a long single-stranded DNA tail.

In addition, the sequence complementary to the target nucleic acid binding sequence refers to a sequence in which at least a part of the target nucleic acid binding sequence of the first single strand can form a complementary binding.

In an aspect of the present invention, the first single strand and the second single strand can independently have a length of 25 to 40 nucleotides, but not always limited thereto.

In addition, at least a part of the first single strand is complementary to at least a part of the second single strand, and can have a duplex of 15 to 30 nucleotides in length, for example.

Furthermore, the target nucleic acid binding sequence of the first single strand is a sequence capable of binding to the target nucleic acid through complementary base pairing, and can be, for example, 20 to 25 nucleotides in length.

In one embodiment of the present invention, the target nucleic acid binding sequence can be designed as a sequence complementary to the target nucleic acid sequence, and some bases can be substituted, deleted, or added within a range that does not affect the binding force with the target nucleic acid.

In one embodiment of the present invention, the DNAzyme sequence of the second single strand can be used without limitation as long as it shows a peroxidase activity.

In one embodiment of the present invention, whether the DNAzyme sequence was activated by dissociating the second single strand from the duplex molecular beacon of the present invention by the target nucleic acid (miRNA) was investigated by polyacrylamide gel electrophoresis and DNAzyme catalyzed peroxidation. As a result, it was confirmed that the DNAzyme sequence was activated only when the target nucleic acid (miRNA) was present and catalyzed the oxidation of ABTS.

In an aspect of the present invention, the DNAzyme blocking sequence can be 3 to 10 nucleotides in length, and preferably 4 nucleotides in length, but not always limited thereto.

In addition, the DNAzyme blocking sequence of the first single strand can be determined by comparing the peroxidase activity of the DNAzyme activated in the presence of the target nucleic acid.

Furthermore, the sequence complementary to the target nucleic acid binding sequence of the second single strand can be 10 to 20 nucleotides in length, and can have a sequence complementary to a part of the target nucleic acid binding sequence of the first single strand.

In an aspect of the present invention, each strand of the duplex molecular beacon (dMB) can be 25 to 40 nucleotides in length, preferably the first single strand can be 25 to 30 nucleotides, and the second single strand can be 33 to 38 nucleotides in length.

In addition, at least a part of the first single strand of the duplex molecular beacon (dMB) can be complementary to at least a part of the second single strand, and the molecule can have a duplex of 15 to 30 nucleotides in length, preferably 20 to 23 nucleotides in length.

Furthermore, the duplex molecular beacon (dMB) can have one or more 3' overhangs including 3' overhangs of the first single strand, and the overhangs can be 5 to 20 nucleotides in length.

In an aspect of the present invention, linkers can be further included between the DNAzyme blocking sequence of the duplex molecular beacon (dMB) first single strand and the target nucleic acid binding sequence and between the DNAzyme sequence of the second single strand and the sequence complementary to the target nucleic acid binding sequence.

Herein, the length of the linker of the duplex molecular beacon (dMB) can be 1 to 5 nucleotides, and the base sequence of the linker can be any sequence that is not particularly limited.

In one embodiment of the present invention, the second single strand of the duplex molecular beacon (dMB) is dissociated when bound with the target nucleic acid through 3' overhang of the first single strand, and can form a G-quadruplex DNAzyme (Dz) structure with a long single-stranded DNA tail.

In an aspect of the present invention, the duplex molecular beacon can be as follows.

a) A molecule having a polydioxynucleotide sense strand and a polydioxynucleotide antisense strand, which forms a double-stranded molecule with sticky ends at both ends, the sense strand contains a DNAzyme blocking sequence and a target nucleic acid binding sequence, and the antisense strand contains a sequence complementary to the DNAzyme sequence and the target nucleic acid binding sequence;

b) The DNAzyme blocking sequence of the sense strand has a base sequence of 4 nucleotides complementary to the 5' end of the DNAzyme sequence, which; and c) The antisense strand is complementary to the target nucleic acid binding sequence, but has a sequence of 6-7 nucleotides shorter than that, and is connected with the DNAzyme sequence through a spacer of 2-3 nucleotides.

In an aspect of the present invention, it can be understood that the target nucleic acid comprises DNA or RNA having a sequence at least partially complementary to the first single strand of the duplex molecular beacon. When the target nucleic acid DNA or RNA is present in a sample, the first single strand of the duplex molecular beacon having a complementary sequence is hybridized with the DNA or RNA to become a double-stranded nucleic acid, and the second single strand is dissociated and adsorbed on graphene oxide, and the second single strand functions as DNAzyme on the surface of graphene oxide, so that the target nucleic acid DNA or RNA present in the sample can be detected colorimetrically.

Herein, the target nucleic acid DNA can include DNA encoding a protein or DNA not encoding a protein, but not always limited thereto. For example, the said RNA can include mRNA (messenger RNA), tRNA (transfer RNA), rRNA (ribosomal RNA), sRNA (small RNA), snRNA (small nuclear RNA), scRNA (small cytoplasmic RNA), siRNA (small interfering RNA), or miRNA (microRNA), but not always limited thereto. The said RNA can also include RNA translated into protein, RNA not translated into protein, 5'-untranslated region, 3'-untranslated region, or regulatory RNA, but not always limited thereto.

In an aspect of the present invention, the said RNA can include miRNA, but not always limited thereto. The miRNA may be involved in biological functions in vivo, and can include those used as important biomarkers in diagnosis, treatment, or prognosis of various diseases such as breast cancer, lung cancer, liver cancer, pancreatic cancer, stomach cancer, colon cancer, bone cancer, skin cancer, blood cancer, diabetes, or Alzheimer's disease. For example, the miRNA can be involved in lineage specific differentiation in stem cells, but not always limited thereto.

In an aspect of the present invention, the miRNA can include miRNA-21, miRNA-29a, miRNA-125b, miRNA-155, or miRNA-159, but not always limited thereto. The said miRNA-21, miRNA-29a, miRNA-125b, or miRNA-155 can be expressed in human cells, and the miRNA-159 can be expressed in plant cells, but not always limited thereto. The miRNA-21, miRNA-29a, and miRNA-125b can be expressed in breast cancer cells, but not always limited thereto. For example, the miRNA-21, miRNA-29a, miRNA-125b, or miRNA-155 can be expressed in the breast cancer cell line MDA-MB-231, MDA-MB435 or MCF-7; or in other cancer cells, but not always limited thereto.

Figure 2:
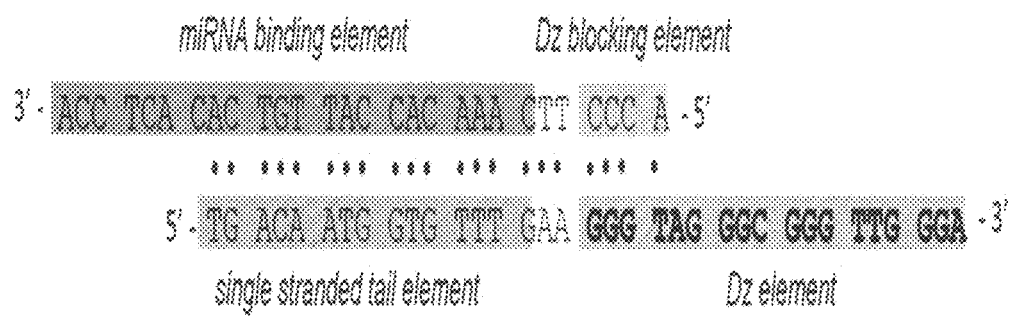
FIG. 2 is a diagram showing the DNA sequences of the target and the duplex molecular beacon (dMB) used in Examples of the present invention.

In a preferred embodiment of the present invention, as shown in FIG. 2, the target nucleic acid is miRNA-122, which can have a sequence of UGG AGU GUG ACA AUG GUG UUU (SEQ. ID. NO: 1). The first single strand can be 3'-ACC TCA CAC TGT TAC CAC AAA CTT CCC A-5' (SEQ. ID. NO: 2), and the second single strand can be 5'-TG ACA ATG GTG TTT GAA GGG TAG GGC GGG TTG GGA-3' (SEQ. ID. NO: 3). Herein, the DNAzyme sequence forming a nucleic acid quadruplex is 5'-GGG TAG GGC GGG TTG GGA-3' (SEQ. ID. NO: 4). In addition, if the DNAzyme sequence forms a nucleic acid quadruplex, it can be included in the present invention, and in particular, if the DNAzyme sequence is capable of forming a G-quadruplex structure, it is included in the present invention.

In a preferred embodiment of the present invention, a DNAzyme sequence comprising 5'-GTGGGGCAT-TGTGGGTGGGTGTGG-3', 5'-GTGGGTAGGGCGGGTTGG-3', 5'-GGTGGTGGTGGTTGTGGTGGTGGTGG-3', or 5'-GGGTTAGGGTTAGGGTTAGGG-3' instead of 5'-GGG TAG GGC GGG TTG GGA-3' can be used.

In an aspect of the present invention, the graphene oxide can be in the form of a single layer sheet, but not always limited thereto. For example, the graphene oxide in the form of a single layer sheet can absorb a large number of nucleic acid probes in a small amount due to its large surface area at the same mass compared to the graphene oxide not in the form of a single layer sheet.

In an aspect of the present invention, the graphene oxide can be in the form of particles having a size of about 10 nm to about 1 μm, but not always limited thereto.

For example, the graphene oxide can be about 10 nm to about 1 μm, about 10 nm to about 700 nm, about 10 nm to about 500 nm, about 10 nm to about 400 nm, about 10 nm to about 300 nm, about 10 nm to about 200 nm, about 10 nm to about 100 nm, about 10 nm to about 50 nm, about 50 nm to about 1 μm, about 100 nm to about 1 μm, about 200 nm to about 1 μm, about 300 nm to about 1 μm, about 400 nm to about 1 μm, about 500 nm to about 1 μm, about 700 nm to about 1 μm, about 200 nm to about 300 nm, or about 400 nm or less, but not always limited thereto.

Since the size of the graphene oxide is small, it can easily pass through the cell membrane and enter into cells together with the second single strand adsorbed on the surface.

In an aspect of the present invention, the target nucleic acid can be present in cells, but not always limited thereto. For example, the cells can include cells cultured fixed to a substrate, cells suspended and cultured in a medium, cells in vivo, cells isolated from a living body, or cells treated for analysis, but not always limited thereto. In addition, the cells can include living cells or dead cells, and can include cells fixed by a fixing solution, but not always limited thereto.

In an aspect of the present invention, the DNAzyme cofactor can be understood to be included in the present invention without limitation as long as it can be used to function as DNAzyme together with the DNAzyme sequence part of the second single strand. In one embodiment of the present invention, the DNAzyme can be one that exhibits peroxidase activity, and the DNAzyme cofactor can be hemin.

In an aspect of the present invention, the composition for detecting nucleic acid can further include a colorimetric reagent.

Herein, the colorimetric reagent can be included in the present invention without limitation, as long as it can exhibit colorimetry by the DNAzyme activity. For example, the colorimetric reagent can include one or more compounds selected from the group consisting of ABTS, OPD, DAB, AEC, TMB, AmplexRed and Homovanilic acid, and one or more peroxides.

In an embodiment of the present invention, the present invention is not limited to a specific theory, but the DNAzyme exhibits peroxidase activity. The DNAzyme can detect colorimetry from one or more selected from the group consisting of the ABTS, OPD, DAB, AEC, TMB, AmplexRed, and Homovanilic acid through a series of oxidation-reduction processes of the at least one peroxide with one or more selected from the group consisting of the ABTS, OPD, DAB, AEC, TMB, AmplexRed, and Homovanilic acid.

In an aspect of the present invention, when the first single strand of the duplex molecular beacon is combined with the target nucleic acid, the second single strand is dissociated from the first single strand, and the DNAzyme sequence and the DNAzyme cofactor of the dissociated second single strand function as DNAzyme to detect the target nucleic acid. The detection signal is amplified from the adsorption of the dissociated second single strand on the graphene oxide.

In a preferred embodiment of the present invention, the amplification of the detection signal can be accomplished by the concentration of the activated DNAzyme on the graphene oxide surface by adsorbing the second single strands on the graphene oxide surface, and the concentration of the detection signal on the graphene oxide surface.

In another embodiment of the present invention, the graphene oxide/second single strand or the graphene oxide/second single strand/DNAzyme cofactor forms a graphene oxide complex, and the detection signal is amplified by concentrating only the graphene oxide complex through a series of filtration or separation processes.

In the present invention, it was confirmed that a graphene oxide complex in a solution was obtained, and centrifugation was performed to obtain a pellet of the graphene oxide complex, from which the signal amplification was excellent proportional to the concentration of the target nucleic acid and quantitative analysis of the target nucleic acid was possible. It was also confirmed that the signal amplification was excellent proportional to the concentration of the target nucleic acid and quantitative analysis of the target nucleic acid was possible when the paper (in addition to paper, substrates having a filtering function are all included in the present invention) capable of filtering the graphene oxide complex, and permeating other target nucleic acids or substances having the size of the duplex molecular beacon was used, so that it could be applied to point-of-care testing (POCT).

The present invention also provides a method for detecting a target nucleic acid with an amplified detection signal, wherein the duplex molecular beacon is formed by complementarily conjugating the first single strand containing the target nucleic acid binding sequence and the second single strand containing the DNAzyme sequence at least in part, comprising the following steps:

obtaining a mixture by mixing a sample containing a target nucleic acid and a duplex molecular beacon;

adding graphene oxide to the mixture; and obtaining a concentrated graphene oxide complex by filtering or separating the mixture.

Hereinafter, the method for detecting a target nucleic acid with an amplified detection signal will be described in detail step by step.

The step of obtaining a mixture by mixing a sample containing a target nucleic acid and a duplex molecular beacon can be understood as a step of dissociating the second single strand by combining the first single strand of the duplex molecular beacon and the target nucleic acid.

Herein, it can be understood that the first single strand and the target nucleic acid are hybridized from the part having a complementary sequence of at least a portion to dissociate the second single strand. On the other hand, the definitions and descriptions of each target nucleic acid, the first single strand and the second single strand are the same as described above, and thus will be omitted here.

The step of adding graphene oxide can be understood as adding graphene oxide (GO) to the obtained mixture. This step can also be understood as a step of obtaining a graphene oxide complex by adsorbing the dissociated second single strand of the mixture to the graphene oxide. Since the dissociated second single strand has a DNAzyme sequence, it can be modified into a form capable of functioning as DNAzyme in a free state and a state adsorbed on graphene oxide. For example, it can exhibit the shape of a nucleic acid quadruplex, specifically a guanine quadruplex. In particular, the second single strand nucleic acid quadruplex shape, that is, the DNAzyme sequence is exposed on the graphene oxide surface, and it functions as DNAzyme on the graphene oxide surface along with the DNAzyme cofactor. Meanwhile, a more detailed description of the graphene oxide size and the like is the same as described above, and thus will be omitted here.

The step of obtaining a concentrated graphene oxide complex by filtering or separating the mixture can be understood as a step of concentrating the graphene oxide complex only through a series of filtration or separation steps and amplifying the detection signal.

It can be understood that the graphene oxide complex is concentrated through the filtration or separation, and a colorimetric detection signal is amplified therefrom.

In a preferred embodiment of the present invention, it was confirmed that a graphene oxide complex in a solution was obtained, and centrifugation was performed to obtain a pellet of the graphene oxide complex, from which the signal amplification was excellent proportional to the concentration of the target nucleic acid and quantitative analysis of the target nucleic acid was possible.

In another preferred embodiment of the present invention, it was also confirmed that the signal amplification was excellent proportional to the concentration of the target nucleic acid and quantitative analysis of the target nucleic acid was possible when the paper (in addition to paper, substrates having a filtering function are all included in the present invention) capable of filtering the graphene oxide complex, and permeating other target nucleic acids or substances having the size of the duplex molecular beacon was used, so that it could be applied to point-of-care testing (POCT).

In an aspect of the present invention, the method for detecting a target nucleic acid with an amplified detection signal can further include a step of adding a DNAzyme cofactor to the mixture.

Herein, the step of adding a DNAzyme cofactor can be understood as a step of forming a graphene oxide complex (graphene oxide/second single strand/DNAzyme cofactor) capable of functioning as DNAzyme together with the second single strand DNAzyme sequence (eg, nucleic acid quadruplex) adsorbed on the graphene oxide surface. Meanwhile, the descriptions of the DNAzyme cofactor, nucleic acid quadruplex, and the like are the same as described above, and thus will be omitted here.

In an aspect of the present invention, the method for detecting a target nucleic acid with an amplified detection signal can further include a step of adding a colorimetric reagent to the concentrated graphene oxide complex.

The step of adding a colorimetric reagent can be understood as a step of adding a colorimetric reagent comprising one or more compounds selected from the group consisting of ABTS, OPD, DAB, AEC, TMB, AmplexRed and Homovanilic acid, and one or more peroxides to detect colorimetry from the graphene oxide complex (graphene oxide/second single strand/DNAzyme cofactor). Although the present invention is not limited to a specific theory, this step can be understood as a step in which colorimetric change appears through the oxidation-reduction reaction of the colorimetric reagent by DNAzyme of the graphene oxide complex.

On the other hand, in the method for detecting a target nucleic acid with an amplified detection signal of the present invention, it should be understood that the changes and modifications apparent to those skilled in the art, such as the order of detailed condition steps of each step, are also included in the present invention.

In addition, the present invention provides a kit for detecting nucleic acid with an amplified detection signal containing a composition comprising graphene oxide, duplex molecular beacon and DNAzyme cofactor, wherein the duplex molecular beacon is formed by complementarily conjugating the first single strand containing the target nucleic acid binding sequence and the second single strand containing the DNAzyme sequence at least in part, and the second single strand is separated from the first single strand and adsorbed to graphene oxide to form a graphene oxide complex in the presence of the target nucleic acid.

In an aspect of the present invention, the kit can further include a colorimetric reagent. Herein, the colorimetric reagent can be included in the present invention without limitation, as long as it can exhibit colorimetry by the DNAzyme activity. For example, the colorimetric reagent can include one or more compounds selected from the group consisting of ABTS, OPD, DAB, AEC, TMB, AmplexRed and Homovanilic acid, and one or more peroxides.

In an aspect of the present invention, the kit can further include a device capable of obtaining a concentrated graphene oxide complex by filtering or separating the mixture obtained by mixing the composition and the target nucleic acid.

In a preferred embodiment of the present invention, the device can be a substrate that retains the graphene oxide complex and filters smaller materials than the complex. In addition, the device is included in the present invention as long as it can filter or isolate the graphene oxide complex concentrated from the mixture, and can included in the kit.

Herein, the substrate can be a paper such as a filter paper that can filter the graphene oxide complex from the mixture.

Hereinafter, the present invention will be described in detail by the following examples.

However, the following examples are only for illustrating the present invention, and the contents of the present invention are not limited thereto.

<Example 1> Preparation of DNAzyme Activation System by miRNA

To prepare the duplex molecular beacon (dMB) comprising a miRNA binding sequence and an inactive DNAzyme sequence as a DNAzyme activation system by miRNA, 2.5 µL of 100 µM sense strand DNA was mixed with the same amount of antisense strand DNA in 1× buffer. The mixture was then annealed by heating at 90° C. for 5 minutes and slowly cooling at room temperature for 1 hour. As a target, miR-122 was selected because of its specific expression in the liver and strong association with liver damage. Particularly, the duplex molecular beacon (dMB) structure was designed as a 7-nt toehold region according to the previous research (D. Y. Zhang, S. X. Chen, P. Yin, Optimizing the specificity of nucleotide hybridization, Nat. Chem, 4(2012) 208-214) on the toehold-mediated strand displacement (TMSD). The sense strand of the duplex molecular beacon (dMB) is composed of a miRNA binding sequence and a DNAzyme blocking sequence connected by a 2-adenine spacer. The length of the DNAzyme blocking sequence (Dz blocking element) was determined to be 4 nt by comparing the peroxidase activity of the DNAzyme activated in the presence of the target nucleic acid. The antisense strand consists of a G-quadruplex DNAzyme sequence, a 2-thymine spacer, and a single tail element (=partial miR-122 imitation sequence). By hybridizing the two strands, formation of a G-quadruplex structure for DNAzyme activity was blocked, and 7 nucleotide toeholds were prepared for the strand displacement by miRNA-122 (FIG. 2).

<Experimental Example 1> Confirmation of DNAzyme Activation by Target miRNA

<1-1> Polyacrylamide Gel Electrophoresis Analysis

Whether the DNAzyme was activated from the duplex molecular beacon of the present invention by target miRNA was confirmed by polyacrylamide gel electrophoresis and DNAzyme catalyzed peroxidation.

Particularly, mixtures of 10 pmol duplex molecular beacon, 0-20 pmol target nucleic acid and each polynucleotide control were prepared on 12% native polyacrylamide gel, and electrophoresis was performed at 100 V for 1 hour.

Figure 3:
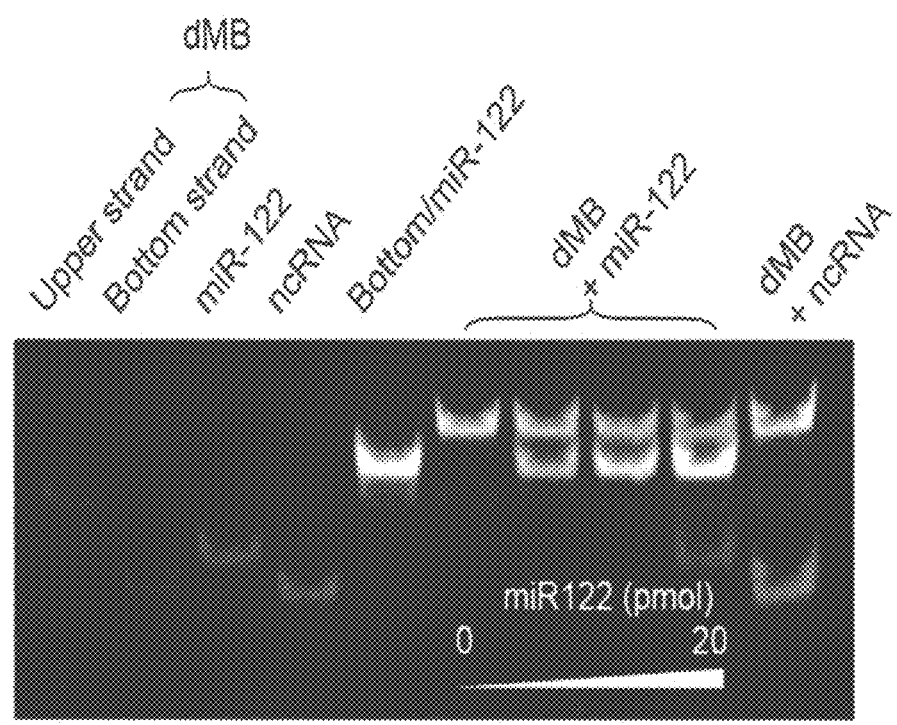
FIG. 3 is a diagram showing the results of polyacrylamide electrophoresis of sequence-specific toehold mediated strand displacement (TMSD) using duplex molecular beacon, miRNA and non-complementary (ncRNA).

As a result, only miRNA-122 produced a new band in proportion to the concentration of RNA in 1×Dz buffer, whereas non-specific RNA did not affect the original dMB band (FIG. 3). This suggests that the sequence-specific miRNA-122 can induce the strand displacement of the duplex molecular beacon (dMB) and replace the DNAzyme strand.

<1-2> Sequence Specific Colorimetric Analysis Using Duplex Molecular Beacon (dMB)

Sequence-specific colorimetric analysis was performed using the duplex molecular beacon (dMB) treated with miRNA-122 and 2,2'-azino-bis (3-ethyl benzothiazoline-6 sulfonic acid (ABTS)) as a colorimetric substrate (4 µM hemin, 5 mM ABTS, 0.5 mM $H_2O_2$).

Particularly, 50 pmol duplex molecular beacon was mixed in 1×buffer (20 mM Tris buffer (pH 7.2), 20 mM KCl and 100 mM NaCl) containing the target nucleic acid, and after 30 minutes, 4 pmol hemin, 5 nmol ABTS, and 0.5 nmol $H_2O_2$ were added thereto.

Figure 4:
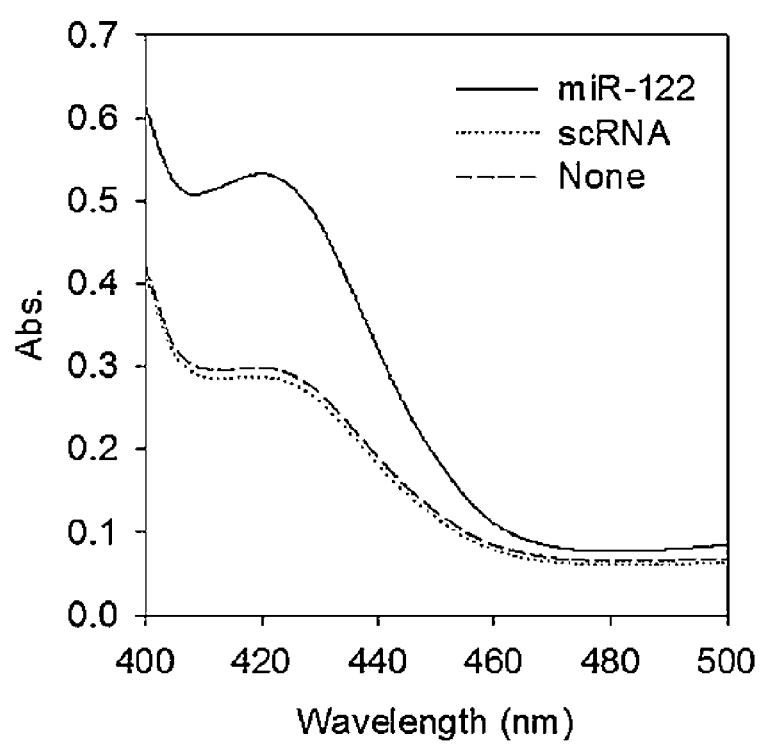
FIG. 4 is a graph showing the absorbance spectrum of a duplex molecular beacon (dMB) and a target RNA mixture in the presence of hemin, ABTS, and $H_2O_2$.

As a result, it was confirmed that the absorbance at 420 nm (A420) was increased as the colorless ABTS was oxidized to green ABTS cations. In contrast, there was little change in A420 in the solution containing only scrambled RNA or duplex molecular beacon (dMB) (FIG. 4). The above results suggest that DNAzyme is activated only in the presence of a sequence-specific target and catalyzes the oxidation of ABTS.

<Experimental Example 2> Optimization of the Amount of GO Required to Capture the DNAzyme Strand Prior to the experiment for colorimetric analysis using the graphene oxide net (GONET) method of the present invention, it was intended to determine the optimal amount of graphene oxide (GO) required to capture the DNAzyme strand dissociated from the duplex molecular beacon.

Graphene oxide was prepared by the known synthetic protocol (Y. K. Kim, D. H. Min, The structural influence of graphene oxide on its fragmentation during laser desorption/ionization mass spectrometry for efficient small-molecule analysis, Chemistry 21(2015) 7217-7223), and confirmed by scanning electron microscopy (SEM), atomic force microscopy (AFM), RAMAN spectroscopy and Fourier transform infrared spectroscopy (FT-IR). Single strand DNAzyme (50 µmol) was treated for 20 minutes in 1×Dz buffer containing varying amounts of graphene oxide (0-10 µg). The graphene oxide adsorbed single strand DNAzyme was spun down to obtain a supernatant, which was mixed with a colorimetric reagent (4 µmol hemin, 5 nmol ABTS, 0.5 nmol $H_2O_2$).

Figure 5:
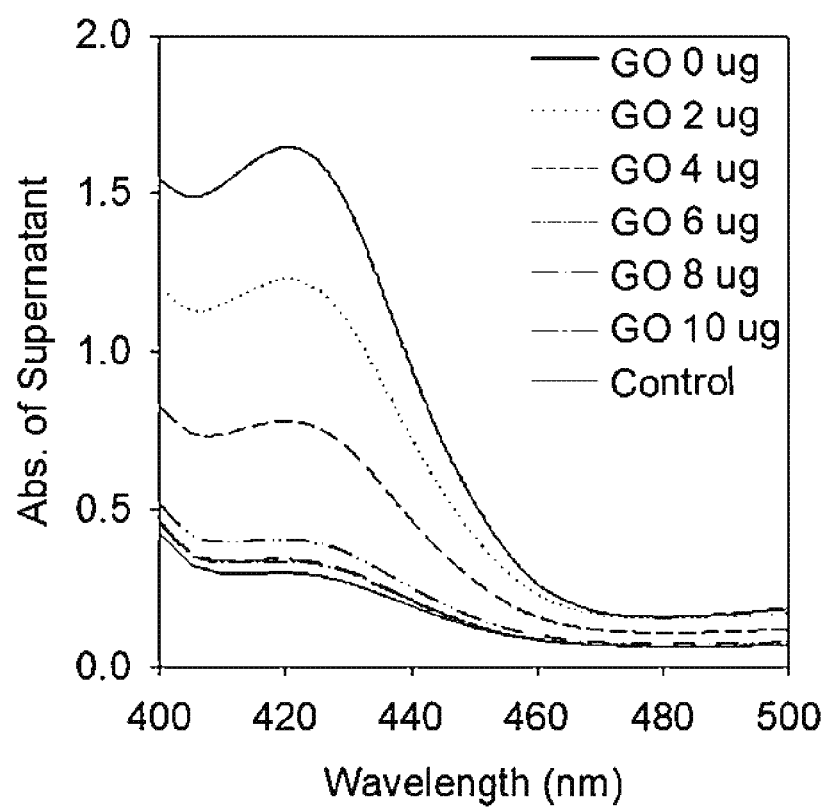
FIG. 5 is a graph showing the absorbance spectrum of the supernatant measured after spin-down of the 50 pmol DNAzyme captured by various concentrations of graphene oxide.
Figure 6:
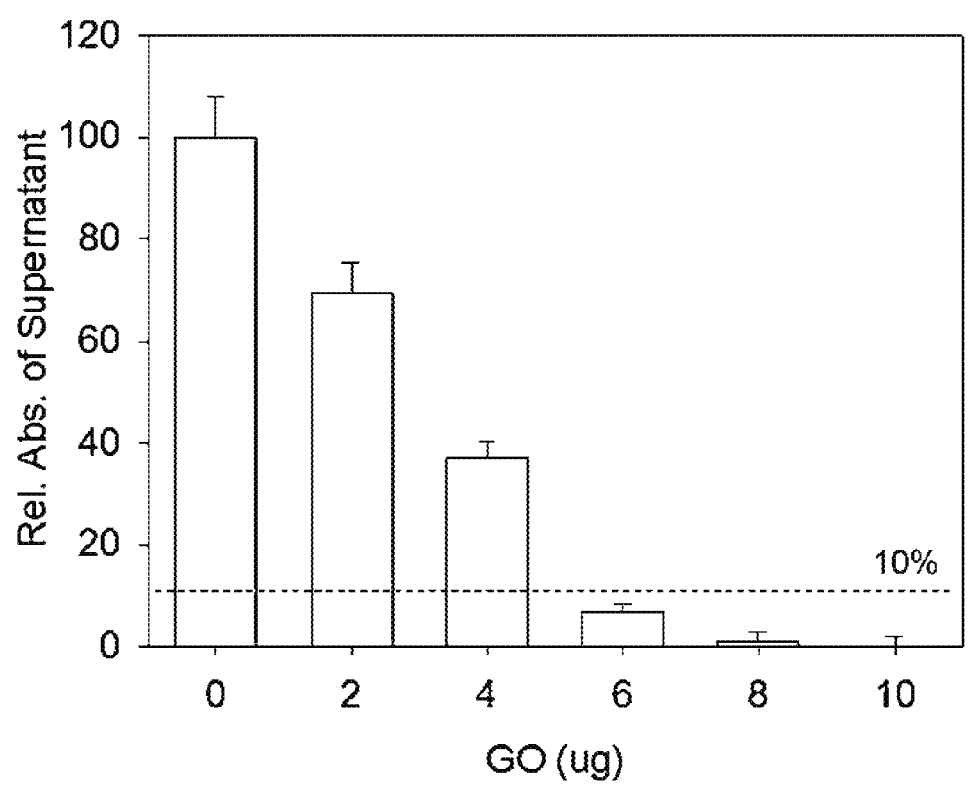
FIG. 6 is a graph showing the relative absorbance changes of the supernatant according to the addition of GO.

As a result, A420 of the supernatant was decreased as the concentration of the graphene oxide was increased due to the adsorption of DNAzyme and graphene oxide, and more than 90% of A420 of the initial supernatant was reduced in the presence of 6 µg of graphene oxide (FIG. 5). High concentration of graphene oxide increased the efficiency of DNAzyme capture, but the high concentration of graphene oxide itself affected the background color observed with the naked eye. The adsorption of DNAzyme by graphene oxide was confirmed by quenching, which was consistent with the results of colorimetric optimization experiments.

Therefore, the optimal amount of graphene oxide (GO) required to capture the 50 µmol DNAzyme strand dissociated from the duplex molecular beacon was confirmed to be 6 µg.

<Experimental Example 4> Performance Evaluation of GONET-Based Colorimetric miRNA Assay To evaluate the performance of colorimetric miRNA assay using the graphene oxide net (GONET) method, DNAzyme activation by the target miRNA and DNAzyme capture using the graphene oxide net (GONET) were performed in a solution.

Particularly, miR-122 was treated to 500 µl of 1×Dz buffer (20 mM Tris buffer (pH 7.2), 20 mM KCl and 100 mM NaCl) containing 100 nM duplex molecular beacon (dMB) for 30 minutes. After 6 µg of graphene oxide was added to the solution to capture the activated DNAzyme, the mixture was centrifuged at 15000 rpm for 20 minutes, and the supernatant was removed. The graphene oxide pellet was resuspended in 100 µL of 1× buffer, to which 4 nmol hemin, 5 nmol ABTS, 0.5 nmol $H_2O_2$ and a colorimetric reagent were added to develop color.

Figure 7A:
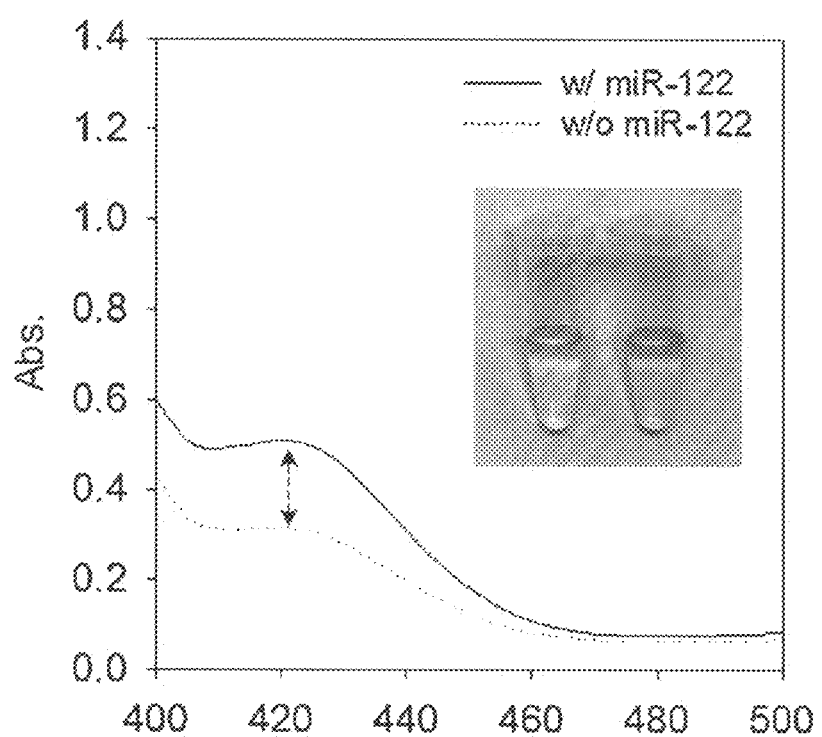
FIGS. 7a to 7b is a set of graphs showing the absorbance spectrum of a duplex molecular beacon (dMB) and RNA mixture measured using a basic colorimetric method after treating the mixture with a colorimetric reagent for 30 minutes (a), and the amount of increase in colorimetry (A420) over time (b).
Figure 7B:
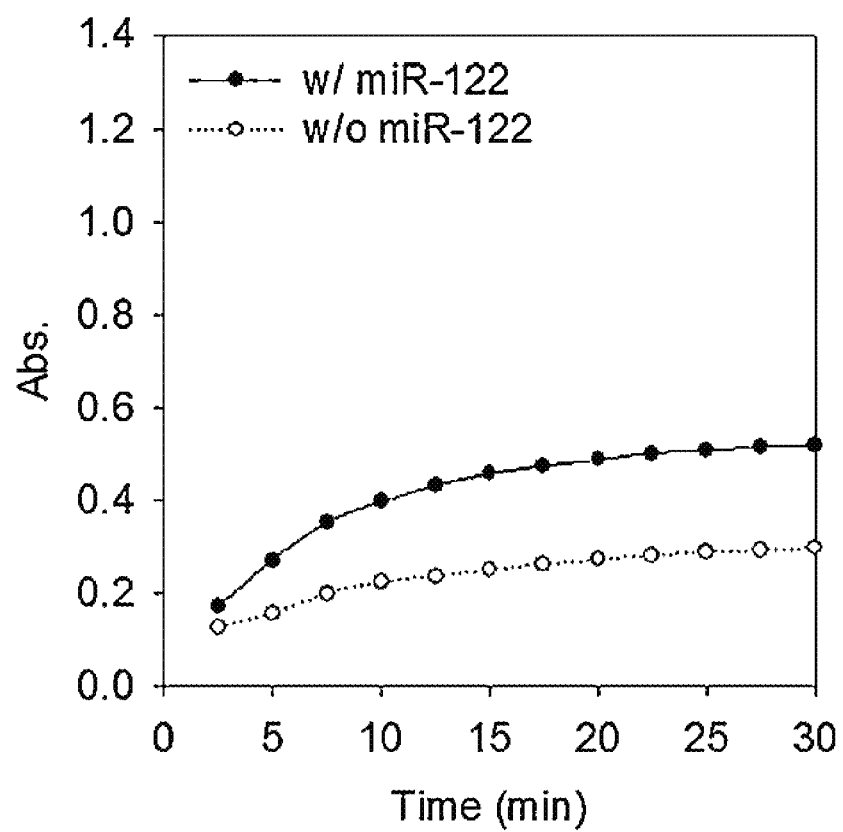
Figure 8A:
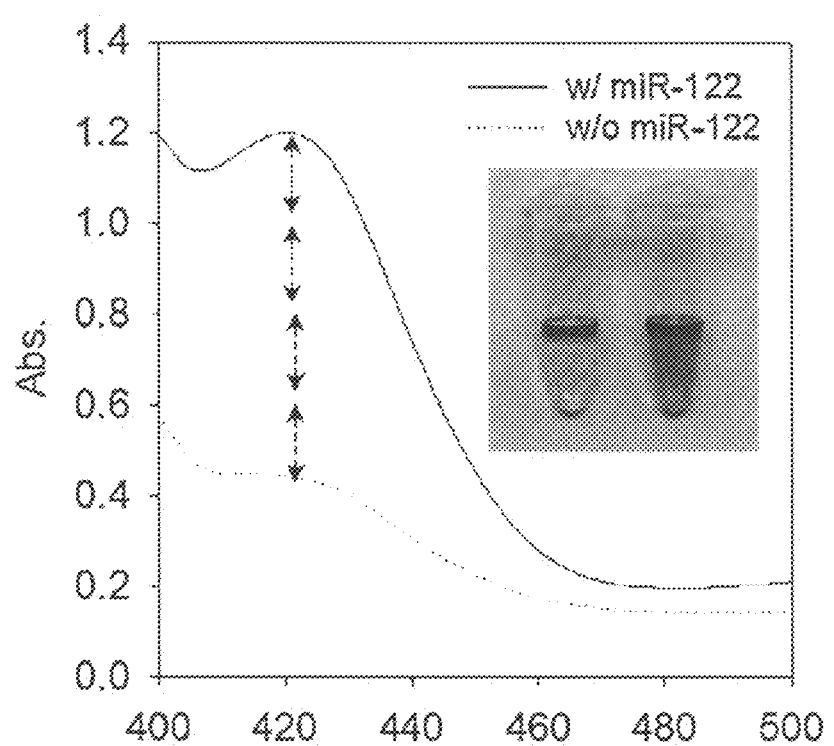
FIGS. 8a to 8b is a set of graphs showing the absorbance spectrum of a duplex molecular beacon (dMB) and RNA mixture measured using a colorimetric method using the GONET of the present invention after treating the mixture with a colorimetric reagent for 30 minutes (a), and the amount of increase in colorimetry (A420) over time in an improved colorimetric analysis using GONET (b).
Figure 8B:
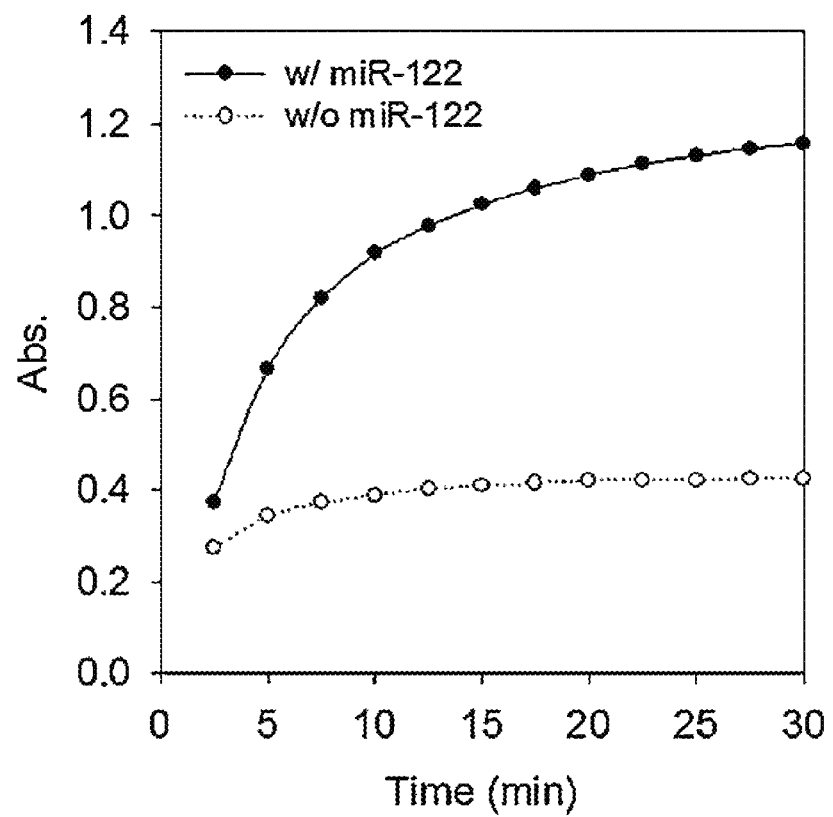

As a result, the sample containing miR-122 showed green color over time compared to the control group without the target nucleic acid regardless of the treatment of graphene oxide (FIGS. 7a to 7b). However, in the sample treated with graphene oxide, A420 was about 4 times higher, and it was confirmed that the signal amplification by aggregating the activated DNAzyme that can be clearly detected. The samples treated with graphene oxide showed dark green shades that were easily distinguishable to the naked eye (FIGS. 8a to 8b).

Thereafter, miRNA detection using the graphene oxide net (GONET) was repeated using the two other representative predictive biomarkers miR-21 and let-7a.

The duplex molecular beacons for these two miRNAs were prepared by simply modifying the miRNA binding sequence and its partially complementary sequence based on the sequence.

As a result, under the same experimental conditions, the samples treated with the graphene oxides for miR-21 and let-7a showed 3.2 and 5.2 times increased green, respectively. These results support that the graphene oxide net (GONET) is a simple and highly efficient method for improving the colorimetric detection signal.

<Experimental Example 5> Determination of Analysis Limit According to the Target Nucleic Acid Concentration To determine the analysis limit according to the target nucleic acid concentration (LOD), colorimetric analysis using GONET was performed on miR-122 at various concentrations.

100 nM of the duplex molecular beacon (dMB) was treated to various concentrations of miR-122, to which graphene oxide was added, and a colorimetric reagent was added to develop color.

Figure 9:
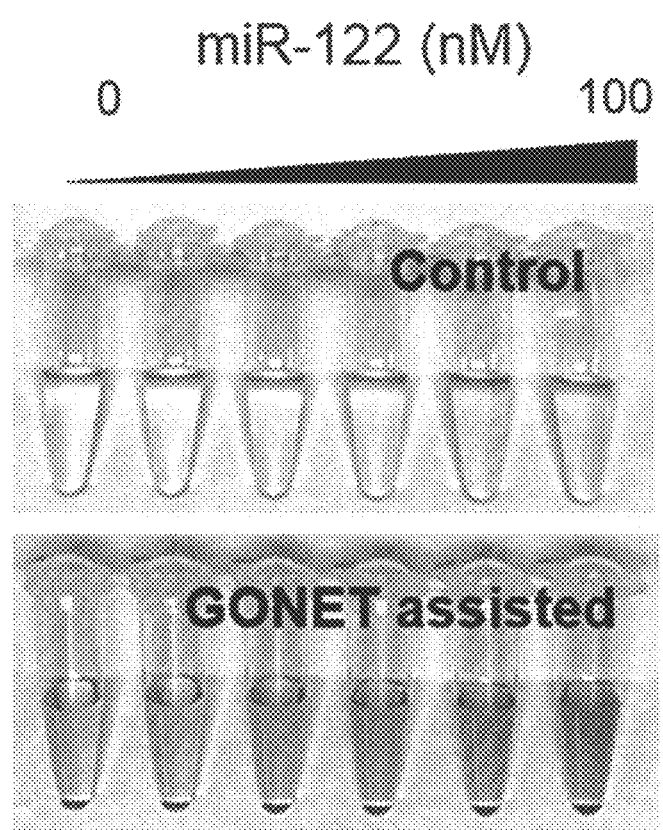
FIG. 9 is a diagram showing the concentration-dependent colorimetric changes of miRNA in the control group non-treated with GONET and the experimental group treated with GONET in the presence of hemin, ABTS and $H_2O_2$.
Figure 10:
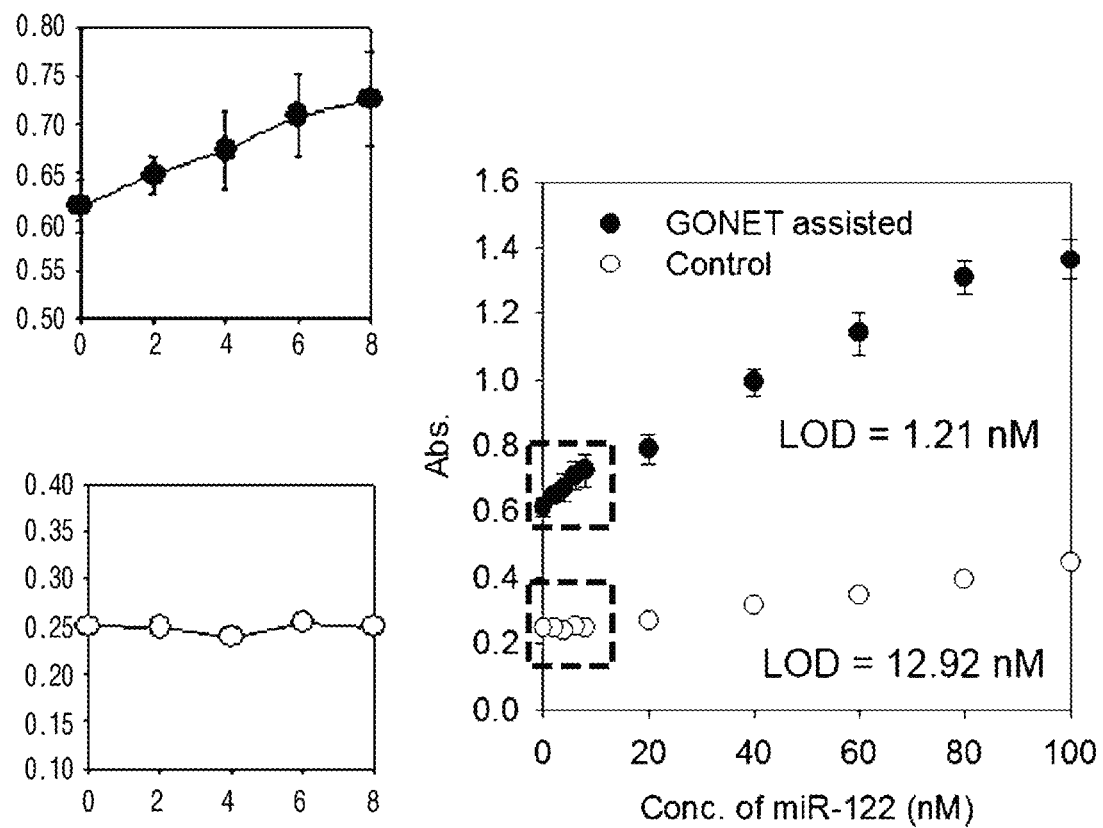
FIG. 10 is a set of graphs showing the analysis limits according to the concentration of target miRNA in the control group non-treated with GONET and the experimental group treated with GONET in the presence of hemin, ABTS and $H_2O_2$.

As a result, the DNAzyme activated by miR-122 without treatment with graphene oxide, the control group, showed no significant difference in color as the concentration of miR-122 increased, and showed only a slight increase in absorbance (FIG. 9). The control group showed linearity at the high concentration of the target RNA (>10 nM) with the analysis limit of 12.92 nM (LOD=3.3 (SD/S) (SD: standard deviation, S: slope of calibration curve)). The graphene oxide treated sample showed dark green color gradually as the miR-122 concentration was increased, and a significant increase in the A420 value was confirmed. The analysis limit (LOD) was 1.21 nM, which was 10 times lower than that of the control group (FIG. 9).

As a result, it was confirmed that the method for detecting a target nucleic acid with an amplified detection signal according to the present invention was sensitive to the target nucleic acid at a lower concentration, and also could confirm the amplification of the colorimetric detection signal as the target nucleic acid concentration was increased, and thus can be used in a quantitative analysis of the target nucleic acid.

<Experimental Example 6> Application of GONET System to Paper Sensor

The graphene oxide net (GONET) method was applied to paper to be used directly for high-efficient point-of-care testing (POCT).

Particularly, a mixture of the duplex molecular beacon (dMB) pre-treated with miR-122 (~10 nM), graphene oxide and hemin was applied to the paper surface.

Figure 11:
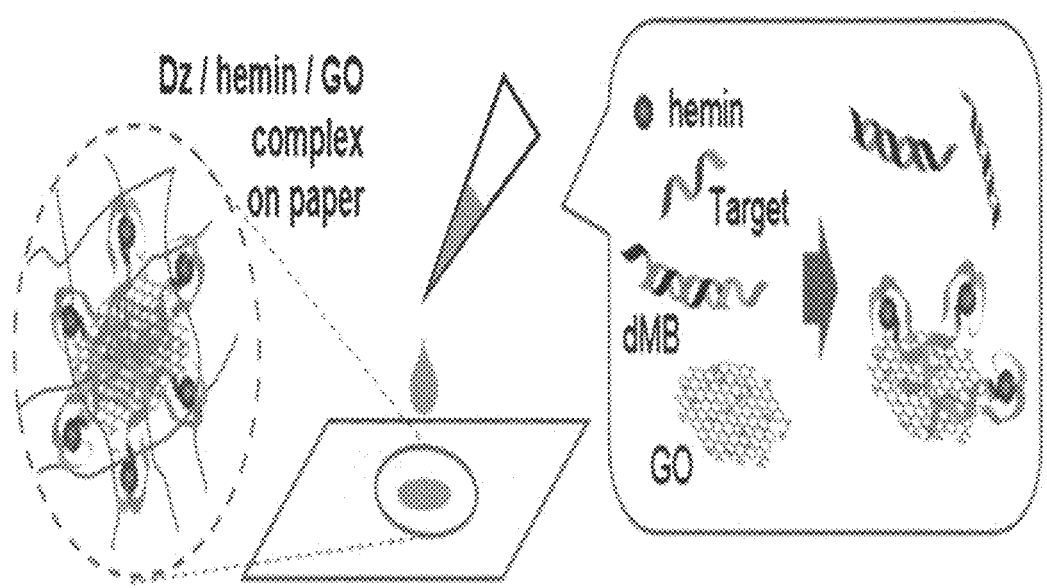
FIG. 11 is a schematic diagram showing the paper sensor based on GONET.

The graphene oxide is a two-dimensional material that is larger than most biomolecules such as DNA or RNA. So the target DNAzyme molecule (graphene oxide complex) had accumulated green in the selected area of the paper on which the graphene oxide solution was dropped (FIG. 11).

Figure 12:
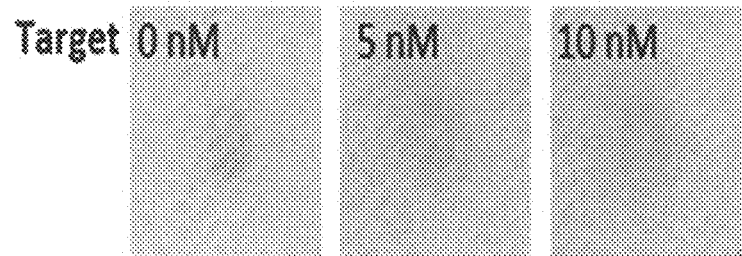
FIG. 12 is a diagram showing the difference in color change of paper when the miRNA concentration was very low in the control group non-treated with GONET and the experimental group treated with GONET in the presence of ABTS and $H_2O_2$.
Figure 12:
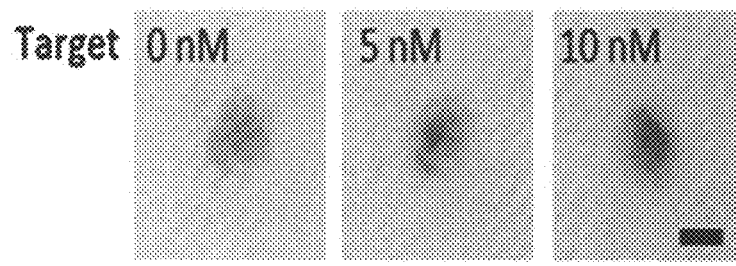

When the graphene oxide was not treated, not only DNAzyme molecules but also other DNA or RNA molecules flowed on the paper, so green color was rarely observed when the colorimetric reagent was applied. On the other hand, when the graphene oxide was treated, the DNAzyme strand captured by the graphene oxide was fixed at a specific site (on the paper) as intended, and the color was changed from pale green to dark green depending on the concentration of miR-122 in a few minutes upon application of the colorimetric reagent (FIG. 12).

In addition, the site-specific deposition of DNAzyme molecules and the corresponding color development were confirmed using GONET solution instead of round spots.

Figure 13:
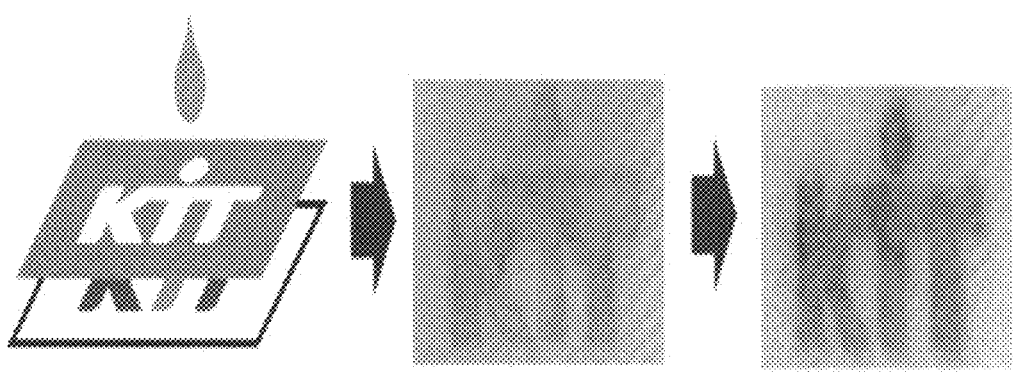
FIG. 13 is a diagram showing the unique color change of GONET spots on paper when the target miRNA concentration was extremely low in the presence of ABTS and $H_2O_2$.

When the activated graphene oxide was applied to the paper, a light brown Dz/GO complex was deposited on the paper according to the shape of the letters. When the graphene oxide was treated after the colorimetric reagent treatment, the green color was clearly seen in a few minutes, and the characters without graphene oxide treatment were almost unrecognizable with the naked eye (FIG. 13).

These results indicate that the graphene oxide net (GONET) method not only forms a clear detection point on the paper, but also improves detection performance by condensing the activated DNAzyme molecules at a point capable of controlling the size and shape.

As a result, it was confirmed that the method for detecting a target nucleic acid with an amplified detection signal according to the present invention is useful for fast and accurate point-of-care testing (POCT) on paper together with the amplified detection signal.

What is claimed is:

1. A method for detecting a target nucleic acid with an amplified detection signal, comprising the following steps:
   (a) obtaining a mixture by mixing a sample containing the target nucleic acid and a duplex molecular beacon, wherein the duplex molecular beacon is formed by complementarily conjugating a first single strand containing a target nucleic acid binding sequence and a second single strand containing a DNAzyme sequence at least in part;
   (b) adding graphene oxide to the mixture, wherein the second single strand of the duplex molecular beacon dissociates from the first single strand when the target nucleic acid is present in the sample and adsorbs to the graphene oxide, thereby generating a graphene oxide complex;
   (c) obtaining a concentrated graphene oxide complex by filtering or separating the mixture; and
   (d) detecting a colorimetric signal of the concentrated graphene oxide complex to detect the target nucleic acid, wherein the colorimetric signal is amplified due to concentration of the graphene oxide complex in step (c).

2. The method for detecting a target nucleic acid with an amplified detection signal according to claim 1, wherein the method further includes a step of adding a DNAzyme cofactor to the mixture.

3. The method for detecting a target nucleic acid with an amplified detection signal according to claim 1, wherein the method further includes a step of adding a colorimetric reagent to the concentrated graphene oxide complex.

4. The method for detecting a target nucleic acid with an amplified detection signal according to claim 1, wherein an amplified colorimetric detection signal is obtained from the graphene oxide complex concentrated by filtration or separation.

5. The method for detecting a target nucleic acid with an amplified detection signal according to claim 4, wherein the filtration is performed on a substrate that retains the graphene oxide complex and filters smaller materials than the complex.

6. The method for detecting a target nucleic acid with an amplified detection signal according to claim 4, wherein the separation is to obtain a concentrated graphene oxide complex pellet through centrifugation.

7. The method for detecting a target nucleic acid with an amplified detection signal according to claim 3, wherein the colorimetric reagent comprises one or more compounds of ABTS, OPD, DAB, AEC, TMB, AmplexRed and Homovanilic acid; and one or more peroxides.

8. The method for detecting a target nucleic acid with an amplified detection signal according to 1, wherein the target nucleic acid includes DNA or RNA.

9. The method for detecting a target nucleic acid with an amplified detection signal according to 2, wherein the DNAzyme cofactor is hemin.

10. The method for detecting a target nucleic acid with an amplified detection signal according to claim 1, wherein the graphene oxide is in the form of particles having a size of 10 nm to 1 μm.

* * * * *

SEQUENCE LISTING

<160> NUMBER OF SEQ ID NOS: 4

<210> SEQ ID NO 1
<211> LENGTH: 22
<212> TYPE: RNA
<213> ORGANISM: Artificial Sequence
<220> FEATURE:
<223> OTHER INFORMATION: purchased from Bioneer (Daejeon, Korea)

<400> SEQUENCE: 1
uggaguguga caaugguguu ug                                              22

<210> SEQ ID NO 2
<211> LENGTH: 28
<212> TYPE: DNA
<213> ORGANISM: Artificial Sequence
<220> FEATURE:
<223> OTHER INFORMATION: purchased from Genotech (Daejeon, Korea)

-continued

```
<400> SEQUENCE: 2
acccttcaaa caccattgtc acactcca                                        28

<210> SEQ ID NO 3
<211> LENGTH: 35
<212> TYPE: DNA
<213> ORGANISM: Artificial Sequence
<220> FEATURE:
<223> OTHER INFORMATION: purchased from Genotech (Daejeon, Korea)

<400> SEQUENCE: 3
tgacaatggt gtttgaaggg tagggcgggt tggga                                35

<210> SEQ ID NO 4
<211> LENGTH: 18
<212> TYPE: DNA
<213> ORGANISM: Artificial Sequence
<220> FEATURE:
<223> OTHER INFORMATION: purchased from Genotech (Daejeon, Korea)

<400> SEQUENCE: 4
gggtagggcg ggttggga                                                   18
```